United States Patent [19]

Demchak

[11] Patent Number: 5,436,355
[45] Date of Patent: Jul. 25, 1995

[54] PROCESS FOR MAKING AVERMECTIN/ZEIN COMPOSITIONS

[75] Inventor: Richard J. Demchak, Langhorne, Pa.

[73] Assignee: Merck & Co., Inc., Rahway, N.J.

[21] Appl. No.: 191,824

[22] Filed: Feb. 3, 1994

[51] Int. Cl.$^6$ .......................................... C07D 315/00
[52] U.S. Cl. .................................................. 549/264
[58] Field of Search ........................ 549/267; 514/450

[56] References Cited

U.S. PATENT DOCUMENTS

| | | | |
|---|---|---|---|
| 4,199,569 | 4/1980 | Chabala et al. | 424/180 |
| 4,427,663 | 1/1984 | Mrozik | 424/180 |
| 4,587,247 | 5/1986 | Linn et al. | 514/222 |
| 4,717,718 | 1/1988 | Eckenhoff et al. | 514/30 |
| 4,874,749 | 10/1989 | Mrozik | 514/30 |
| 4,963,141 | 10/1990 | Eckenhoff | 424/473 |
| 5,215,753 | 6/1993 | Wright et al. | 424/473 |

OTHER PUBLICATIONS

H. Mrozik, et al., J. Organic Chemistry, 1982, 47, pp. 489–492.

John C. Chabala, et al. J. Med. Chem. 1980, 23, pp. 1134–1136.

*Primary Examiner*—C. Warren Ivy
*Assistant Examiner*—A. A. Owens
*Attorney, Agent, or Firm*—Sylvia A. Ayler; Mark R. Daniel

[57] ABSTRACT

Their is disclosed a novel solvent-depletion process for making an avermectin/zein composition and the composition itself, which has excellent photostability and unexpected bioavailability to foliar-feeding insects. The process consists of depleting a dilute acidic, basic or alcoholic solvent from an emulsified solution of avermectin, zein, and dilute solvent.

13 Claims, No Drawings

PROCESS FOR MAKING AVERMECTIN/ZEIN COMPOSITIONS

BACKGROUND OF THE INVENTION

The term avermectin (previously referred to as C-076) is used to describe a series of compounds isolated from the fermentation broth of an avermectin producing strain of Streptomyces avermitilis and derivatives thereof. The morphological characteristics of the culture are completely described in U.S. Pat. No. 4,310,519. The natural avermectin compounds are a series of macrolides, each of which is substituted therein at the 13-position with a 4-(α-L-oleandrosyl)-α-L-oleandrose group. Also known are avermectin compounds or pharmaceutically acceptable salts thereof, wherein the 4″ hydroxy group is replaced with an amino or substituted amino (see U.S. Pat. Nos. 4427663 and 4,874749 and pending U.S. patent application Ser. No. 07/862,035) The preparation and properties of synthetic avermectin aglycones in which the disaccharide moiety has been removed leaving a free hydroxyl group at position 13 have been described by Mrozik et al., J. Org. Chem. 1982, 47, 489–492 and by Chabala et al., J. Med. Chem. 1980, 23 1134–1136. Additionally, U.S. Pat. No. 4,199,569 reveals the 22,23-dihydro avermectin compounds. The avermectin compounds and the instant derivatives thereof have a very high degree of anthelmintic and anti-parasitic activity. The natural compounds have the following general structure:

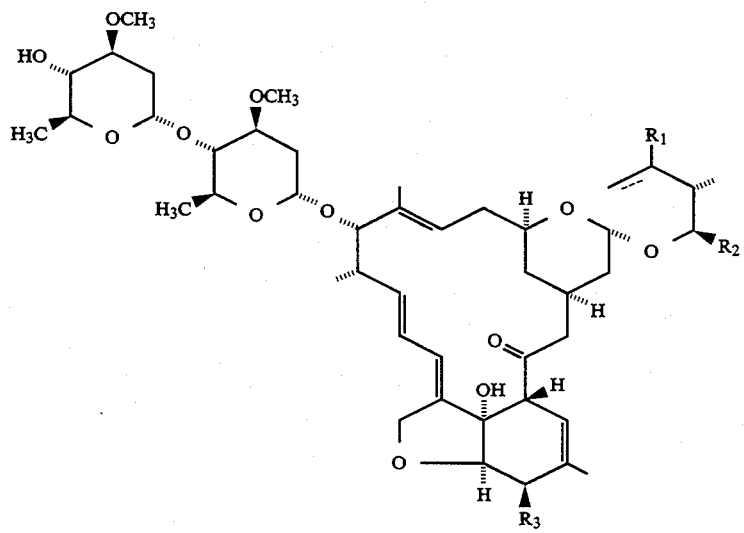

wherein the broken line at the 22,23-position indicates a single or double bond and;

$R_1$ is hydroxy and is present only when said broken line indicates a single bond;

$R_2$ is isopropyl or sec-butyl; and $R_3$ is methoxy or hydroxy.

There are eight major natural avermectin compounds, designated A1a, A1b, A2a, A2b, B1a, B1b, B2a and B2b. These designations are based on the structure of the individual compounds as shown in the following table (referring to the foregoing structural formula).

| Compound | 22,23-bond | $R_1$ | $R_2$ | $R_3$ |
|---|---|---|---|---|
| A1a | double bond | — | sec-butyl | —OH$_3$ |
| A1b | double bond | — | isopropyl | —OH$_3$ |
| A2a | single bond | —OH | sec-butyl | —OH$_3$ |
| A2b | single bond | —OH | isopropyl | —OH$_3$ |
| B1a | double bond | — | sec-butyl | —OH |
| B1b | double bond | — | isopropyl | —OH |
| B2a | single bond | —OH | sec-butyl | —OH |
| B2b | single bond | —OH | isopropyl | —OH |

The avermectins are generally isolated as mixtures of the "a" and "b" components (typically ≧80% "a" and ≦20% "b"). Such compounds differ only in the nature of the $R_2$ substituent and this minor structural difference has been found to have very little effect on the chemical reactivity or biological activity of the compounds. Thus, although the "a" and "b" components can be separated from each other by chromatography this is not necessary and hence is not normally done. The presence of a mixture of "a" and "b" components may be indicated by dropping the "a" or "b" from the designation of the compound. A mixture of avermectin B1a and avermectin B1b is thus referred to as avermectin B1, or abamectin. Alternatively, a slash(/) is inserted between the compound designations to indicate a mixture such as in "B1a/B1b".

The above structural formula is shown without a definitive stereochemistry at certain positions and with a defined stereochemistry at other positions. However, during the course of the synthetic procedures used to prepare such compounds, or using racemization or epimerization procedures known to those skilled in the art, the products of such procedures can be a mixture of stereoisomers. In particular, the stereoisomers at the 13—and 23—positions may be oriented either α—or β—representing such groups being below or above the general plane of the molecule, respectively. In each such case, and at other positions in the molecule, both the α—and β—configurations are intended to be included within the ambit of this invention.

A related family of natural products is known as the milbemycins. The milbemycins have the same macrocyclic ring structure as the avermectins but have no substitution at position 13 and have a methyl or ethyl group at position 25 ($R_2$=methyl or ethyl rather than isopropyl or sec-butyl as in the avermectins). The milbemycins and the fermentation conditions used to prepare them are described in U.S. Pat. No. 3,950,360. Closely related 13-deoxyavermectin aglycones are prepared by chemical modification of the natural avermectins and have been described in U.S. Pat. Nos. 4,171,134 and 4,173,571.

SUMMARY OF THE INVENTION

The instant invention is concerned with a solvent-depletion process for making an avermectin/zein composition and the composition itself, which has excellent photostability and unexpected bioavailability to foliar-feeding insects. A key feature of the process is the depletion of a dilute acidic, basic, or alcoholic solvent (a/b/a solvent) such as acetic acid, propionic acid, lactic acid, ethylene glycol, propylene glycol, diethylene glycol, methyl alcohol, formamide, monoethanolamine, water and the like, most preferably acetic acid, from an emulsified solution of avermectin/zein/a/b/a solvent.

The solution is emulsified in a mineral oil, preferably a mineral oil with a specific gravity of about 0.83 to about 0.88 at 25° C. Under these circumstances, the zein solution forms the dispersed phase while the mineral oil and emulsifier form the continuous phase. The continuous phase is saturated with acetic acid either before or during the emulsification process. The emulsion is pumped and recycled through a suitable semi-permeable membrane that retains the dispersed phase but not the solvent-saturated, continuous phase, which is termed the permeate. Subsequent addition of continuous phase, which has not been solvent saturated, to the emulsion results in depletion of acetic acid from the dispersed phase; ultimately, the dispersed phase consists of avermectin and zein solids suspended in a mineral oil solution. Dodecylamine can optionally be added to the permeate to form the insoluble dodecylamine acetate, in order to recycle the mineral oil.

Thus, it is an object of the present invention to describe such stable avermectin/zein compositions. A further object is to describe the process for the preparation of such compositions. A still further object is to describe the uses of such compositions as anti-parasitic agents and anti-bacterial agents. Still further objects will become apparent from a reading of the following description.

DETAILED DESCRIPTION OF THE INVENTION

The instant composition comprises a solvent-depleted avermectin and zein suspension in mineral oil. The suspension contains a ratio from about 1 to 1 to about 100 to 1 of zein to avermectin, preferably about 3 to 1 to about 25 to 1 of zein to avermectin and from about 60% to about 90% mineral oil.

The avermectin active ingredients and the pharmaceutically acceptable salts thereof such as the benzoate salts in the instant composition have the following structural formula:

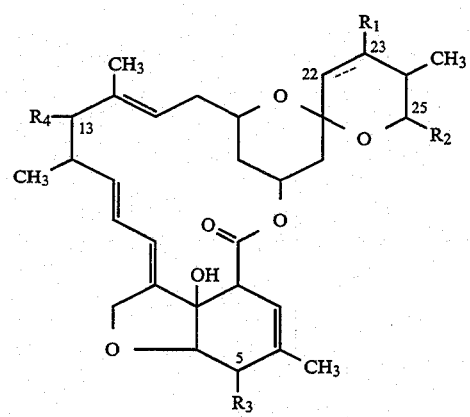

where the broken line indicates a single or a double bond at the 22,23-positions;
$R_1$ is hydrogen or hydroxy, and is hydroxy only when the broken line indicates a single bond;
$R_2$ is alkyl of from 1 to 6 carbon atoms or alkenyl of from 3 to 6 carbon atoms or cycloalkyl of from 3 to 6 carbon atoms;
$R_3$ is hydroxy, methoxy, or $=NOR_5$;
$R_5$ is hydrogen or $C_1$-$C_3$ alkyl; and
$R_4$ is hydrogen, hydroxy, ($C_1$-$C_3$ alkoxy)(—$C_0$-$C_3$ alkoxy)methoxy,

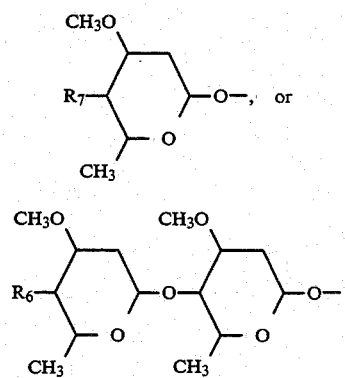

where $R_6$ and $R_7$ is=O, hydroxy, or $R_8R_9$-amino, and R8 and R9 are independently hydrogen, $C_1$-$C_3$ alkyl, $C_2$-$C_3$ alkanoyl, substituted benzenesulfonyl wherein the substituent is halogen or $C_1$-$C_3$ sulfonyl.

The preferred avermectin active ingredients of the instant composition are wherein $R_4$ is:

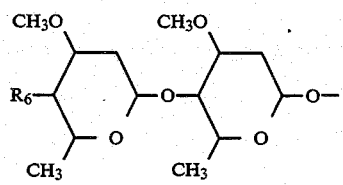

and $R_6$ is as above and the pharmaceutically acceptable salts thereof.

The instant avermectin/zein compositions are prepared using a solvent-depletion process wherein the a mixture of the avermectin/zein/a/b/a solvent is emulsified and then dialyzed to yield the instant stable bioavailable compositions.

PREPARATION OF STARTING MATERIALS

The starting avermectin materials for this invention are disclosed in Albers-Schonberg et al., L Am. Chem. Soc. 1981, 103, 4216-4221 and references cited therein (naturally occurring avermectins), Chabala et al., J. Med. Chem. 1980, 23, 1134-1136 (22,23-dihydro avermectin B1 (ivermectin), 22,23-dihydro avermectin B1-aglycone, U.S. Pat. No. 4,587,247 and U.S. Pat. Nos. 4,427,663 and 4,874,749. Zein is a commercially available protein isolated from corn (See Merck Index 10 ed. page 9918 (1983). The solvents employed are commercially available solvents such as acetic acid, propionic acid, lactic acid, ethylene glycol, propylene glycol, diethylene glycol, methyl alcohol, formamide, monoethanolamine, water and the like.

The active compounds of this invention are potent anti-parasitic agents against external parasitic infestations and are prepared as avermectin/zein compositions with enhanced environmental stability and unexpected bioavailability to foliar-feeding insects.

The avermectin/zein compositions are prepared by dissolving the avermectin compound, from about 1% to about 5%, and the zein from about 5% to about 20% in from about 75% to about 94% of the solvent at ambient temperatures to give a first solution. A small amount of Rhodamine B dye, less than 0.1%, can be added to the first solution to aid in viewing the subsequent emulsion.

A USP Grade mineral oil with a specific gravity of about 0.83 to about 0.88 is used to dissolve from about 5% to about 20% of emulsifier, which is either food-grade lecithin or lecithin fractions to give a second solution. The lecithin fraction/mineral oil solution can be prepared by procedures known to those skilled in the art. For example, 150 grams of food-grade lecithin (>95% acetone insolubles) is added to about 600 mL hexanes, and the components are stirred until most of the lecithin dissolves. If necessary, the solution is allowed to stand to form a sediment and a clear supernatant. Into a 2000 mL flask is added 300 mL of the supernatent and 300 mL ethanol, and the flask is stirred at 40° C. for 1 to 4 hours and then stored at room temperature for 12 to 24 hours. A 300 mL aliquot of the resulting supernatant is removed and discarded, and the solids are redissolved in 600 mL hexanes. The hexane/ethanol fractionation is repeated with the other 300 mL of supernatant, so as to give another hexane solution. The composite solution is evaporated to dryness and the material is stored under vacuum at room temperature. The net weight of the dry material being 110.5 grams, the solid is dissolved in 994.5 grams mineral oil to give 1105 grams of a 10% fractionated lecithin/mineral oil solution.

The first and second solutions are then emulsified with a common homogenizer. Under these circumstances, the zein solution forms the dispersed phase while the mineral oil and emulsifier form the continuous phase. The continuous phase can be diluted with solvent before or during emulsification.

The emulsion is then diffused (dialyzed) through a suitable semi-permeable membrane against mineral oil, which may or may not contain dodecylamine. Alternatively, the emulsion may be pumped through a cross-flow filtration module. The module must allow for sufficient permeate flow for enough time so the depletion process can occur under controlled conditions. A suitable semi-permeable membrane is one with a nominal pore size of 0.2 microns. The semipermeable membrane retains the dispersed phase and releases the solvent saturated continuous phase as permeate. Additional continuous phase which is not saturated with dilute solvent is then added, resulting in the diffusing solvent such as acetic acid, being removed in the permeate with the process continuing until the solvent is depleted from the dispersed phase of the emulsion. The result is a suspension of avermectin and zein solids in a mineral oil solution. The process can be monitored by analyzing the permeate, e.g., by a titration of acetic acid.

The suspension can be analyzed by standard analytical techniques known to those skilled in the art, such as HPLC. The continous phase may contain dissolved avermectin, so the final composition of the dispersed phase may differ from the initial composition. In addition, the dispersed phase may contain both avermectin solid and zein solid, as well as a matrix of avermectin and zein. The analyses are conducted so as to add any dispersed avermectin to that dissolved in the mineral oil. Therefore, the ratio of zein to avermectin in the remaining dispersed phase solids is a measure of the quality of the solvent-depletion process and ranges from about 1 to 1 to about 100 to 1 of zein to avermectin.

The photostability of the avermectin/zein systems are also determined using standard procedures known to those skilled in the art. For example, aliquots of the suspension, in conjunction with an avermectin standard, can be stored under conditions with no light and those which are solar simulated and then evaluated for avermectin content.

The instant compositions are unexpectedly potent antiparasitic agents against ectoparasites, particularly arthropods. Ectoparasites are those parasites which live on the outer surface of the host but still draw nutrients from the host.

Infections by ectoparasitic arthropods such as ticks, mites, lice, stable flies, homilies, blowflies, fleas, and the like are a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus, a stable compound with a broad spectrum of activity and excellent bioavailability is particularly advantageous in the treatment of these diseases. The compounds of this invention have unexpectedly high activity against these parasites, and in addition are also active against *Dirofilaria* in dogs, *Nematospides* and *Syphacia* in rodents, biting insects, and migrating diperous larvae such as *Hypoderma sp.* in cattle, and *Gastrophilus* in horses.

The instant compositions are also useful against ectoparasites which cause parasitic diseases in humans. Ectoparasites which parasitize man include arthropods such as ticks, fleas, mites, lice, and the like and, as with domestic animals, infections by these parasites can result in transmission of serious and even fatal diseases. The instant compositions are active against these ecto parasites and in addition are also active against biting insects and other dipterous pests which annoy humans.

The instant compositions are also useful against common household pests such as *Blatella sp*, (cockroach), *Tineola sp.* (clothes moth), *Attagenus sp.* (carpet beetle),

*Musca domestica* (housefly) and against *Solenopsis Invicta* (imported fire ant).

The compositions are furthermore useful against agricultural pests such as aphids (*Acyrthiosiphon sp.*), locusts, and boll weevils as well as against insect pests which attack stored grains such as *Tribolium sp.* and against immature stages of insects living on plant tissue. The compounds are also useful as a nematocide for the control of soil nematodes and plant parasites such as *Meloidogyne spp*, and lepidopteran pests, which may be agriculturally important.

For use as an antiparasitic agent in animals the instant compounds may be administered topically as a liquid drench or as a shampoo. Topical application of the instant composition is possible through the use of a liquid drench or a shampoo containing the instant compounds as an aqueous suspension. These formulations generally contain a suspending agent such as bentonite and normally will also contain an additional emulsifying agent. Formulations containing from about 0.005 to about 10% by weight of the active ingredient are acceptable. Preferred formulations are those containing from about 0.01 to about 5% by weight of the instant compounds.

The instant compositions are primarily useful as antiparasitic agents for the treatment and/or prevention of ectoparasites such as ticks, mites, lice, fleas and the like. They are also effective in the treatment of parasitic infections of humans. In treating such infections the compounds of these invention may be used individually or in combination with each other or with other unrelated antiparasitic agents. The dosage of the instant compounds required for best results depends on several factors such as the species and size of the animal, the type and severity of the infections, the method of administration and the compound used. Topical administration of the instant compositions containing active compounds at a dose level of from about 0.0005 to about 10 mg per kg of animal body weight, either in a single dose or in several doses spaced a few days apart, generally gives good results. A single dose of one of the instant composition normally gives excellent control however repeat doses may be given to combat re-infection or for parasite species which are unusually persistent. The techniques for administering these compounds to animals are known to those skilled in the veterinary field.

The instant compositions may also be used to combat agricultural pests which attack crops either in the field or in storage. The compositions are applied for such uses as sprays, emulsions and the like either to the growing plants or the harvested crops. The techniques for applying these compounds in this manner are known to those skilled in the agricultural arts.

The following examples is provided in order that this invention might be more fully understood; it is not to be construed as limitative of the invention. The avermectin derivative prepared in the following example is characterized using techniques such as High Performance Liquid Chromatography (HPLC), and the like.

EXAMPLE 1

Lecithin/Mineral Oil/abamectin (as hexanol solvate) Solution

A 10% solution of fractionated lecithin/mineral oil (1105 g) is combined with 100 mg of abamectin and the system stirred at room temperature. The system is then filtered to give a clear lecithin/mineral oil/abamectin solution, which is used as the continuous phase for emulsification of the system.

EXAMPLE 2

Abamectin/Zein Microcapsules

In a 1-liter vessel fitted with a stirrer, homogenizer, and addition funnel which has been cooled to approximately 20° C., is added 500 mL of the 10% lecithin/mineral oil/abamectin solution (continuous phase). Acetic acid (25mL) was then added with stirring. The abamectin/zein solution (dispersed phase) was prepared from 1.00 grams abamectin (as hexanol solvate), glacial acetic acid (46.25 grams), zein (5.00 grams), and Rhodamine B (6 rag); the solution was stirred at room temperature for 24 hours. The dispersed phase solution was then added and the solution emulsified until the temperature rose to 25° C. The addition funnel was then filled with 250 mL of lecithin/mineral oil/abamectin solution which was added over a period of 90 minutes with stirring (this step was once repeated). The resulting emulsion was then pumped and recycled through a 0.2 micron pore size semi-permeable membrane, adding approximately 200 mL of additional lecithin/mineral oil solution during the process. The resulting suspension consisting of avermectin and zein solids in a mineral oil solution (microcapsules ratio of 43 to 1 zein to avermectin) was then isolated from the vessel by vacuum filtration.

EXAMPLE 3

The avermectin microcapsules were compared to abamectin —0.15 EC (control) for photostability under a solar simulator. The zein suspension and EC, each of which contained about 0.01 mG of avermectin B 1a were deposited in petri dishes with an area of about 175 cM$^2$, using cyclohexane as a diluent for both compositions. Four dishes, two for each composition, were placed under a solar simulator, while one dish for each composition was placed in a dark drawer. The dishes were analyzed for avermectin B1a at various times using reversed —phase HPLC and the results showed that avermectin B1a degraded more slowly when combined with zein by the above noted process. The recoveries are shown below:

| Conditions | Recovery (%) | |
|---|---|---|
| Time (Exposure) | Abamectin-0.15 EC | Abamectin/zein |
| 3 days (dark) | 42 | 85 |
| 3 days (light) | 1.5 | 40 |
| 4 days (light) | 0.6 | 38 |

What is claimed is:

1. A solvent-depleted avermectin/zein composition useful for treating plants or animals infected with parasites which comprises avermectin or a pharmaceutically acceptable salt thereof and zein in suspension with a ratio from about 1 to 1 to about 100 to 1 of zein to avermectin and an inert ingredient.

2. The composition of claim 1, wherein the avermectin compound has the structural formula:

[Structure diagram of avermectin skeleton with substituents R1, R2, R3, R4 at positions 13, 22, 23, 25, 5]

where the broken line indicates a single or a double bond at the 22,23-positions;
 $R_1$ is hydrogen or hydroxy, and is hydroxy only when the broken line indicates a single bond;
 $R_2$ is alkyl of from 1 to 6 carbon atoms or alkenyl of from 3 to 6 carbon atoms or cycloalkyl of from 3 to 6 carbon atoms;
 $R_3$ is hydroxy, methoxy, or $=NOR_5$;
 $R_5$ is hydrogen or $C_1$–$C_3$ alkyl; and
 $R_4$ is hydrogen, hydroxy, ($C_1$–$C_3$ alkoxy)(—$C_0$–$C_3$ alkoxy)methoxy,

[Structure: monosaccharide with CH3O, R7, CH3 substituents], or

[Structure: disaccharide with CH3O, R6, CH3, CH3O, CH3 substituents]

where $R_6$ and $R_7$ is=O, hydroxy, or $R_8R_9$-amino, and R8 and R9 are independently hydrogen, $C_1$–$C_3$ alkyl, $C_2$–$C_3$ alkanoyl, substituted benzenesulfonyl wherein the substituent is halogen or C1–$C_3$ sulfonyl.

3. The composition of claim 2 wherein R4 is:

[Structure: disaccharide with CH3O, R6, CH3, CH3O, CH3 substituents]

$R_6$ is as above, the avermectin and zein is suspended in mineral oil and the zein to avermectin ratio is from about 3 to 1 to about 25 to 1.

4. A solvent-depletion process for making avermectin/zein compositions which comprises contacting avermectin or a pharmaceutically acceptable salt thereof and zein with a dilute acidic, basic, or alcoholic solvent, emulsifying the avermectin/zein/solvent solution in a mineral oil with an emulsifier to form a dispersed phase consisting of the avermectin/zein and solvent and a continuous phase consisting of the mineral oil and emulsifier, saturating the continuous phase with the solvent before or during emulsification, pumping and recycling the resulting emulsion through a semi-permeable membrane which retains the dispersed phase and releases the solvent-saturated continous phase as permeate and adding additional continuous phase which is not saturated with solvent, resulting in depletion of the solvent from the dispersed phase, thereby making the avermectin/zein composition suspended in the mineral oil solution.

5. The process of claim 4, wherein the avermectin compound has the structural formula:

[Structure diagram of avermectin skeleton with substituents R1, R2, R3, R4]

where the broken line indicates a single or a double bond at the 22,23-positions;
 $R_1$ is hydrogen or hydroxy, and is hydroxy only when the broken line indicates a single bond;
 $R_2$ is alkyl of from 1 to 6 carbon atoms or alkenyl of from 3 to 6 carbon atoms or cycloalkyl of from 3 to 6 carbon atoms;
 $R_3$ is hydroxy, methoxy, or $=NOR_5$;
 $R_5$ is hydrogen or $C_1$–$C_3$ alkyl; and
 $R_4$ is hydrogen, hydroxy, ($C_1$–$C_3$ alkoxy)(—$C_0$–$C_3$ alkoxy)methoxy,

[Structure: monosaccharide with CH3O, R7, CH3 substituents], or

[Structure: disaccharide with CH3O, R6, CH3, CH3O, CH3 substituents]

where $R_6$ and $R_7$ is=O, hydroxy, or $R_8R_9$-amino, and R8 and R9 are independently hydrogen, $C_1$–$C_3$ alkyl, $C_2$–$C_3$ alkanoyl, substituted benzenesulfonyl wherein the substituent is halogen or $C_1$–$C_3$ sulfonyl.

6. The process of claim 4 wherein R4 is:

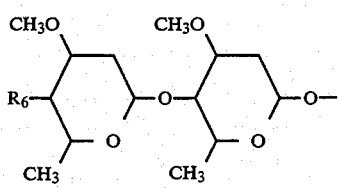

and $R_6$ is as above.

7. The process of claim 4 wherein the dilute acidic, basic or alcoholic solvent belongs to the group consisting of acetic acid, propionic acid, lactic acid, ethylene glycol, propylene glycol, diethylene glycol, methyl alcohol, formamide, monoethanolamine, and water, the semi-permeable membrane has a pore size of about 0.1 to about 0.8 microns and the mineral oil has a specific gravity of about 0.83 to about 0.88 at 25° C.

8. The process of claim 7 wherein the dilute acidic, basic or alcoholic solvent is acetic acid and the semi-permeable membrane has a pore size of about 0.1 to about 0.3 microns.

9. The process of claim 4 wherein dodecylamine can be optionally added to the permeate to form insoluble dodecylamine acetate, which allows the mineral oil to be recycled.

10. The process of claim 4 wherein the emulsifier is food-grade lecithin or fractionated lecithin.

11. The process of claim 4 wherein the emulsifier is fractionated lecithin.

12. A solvent-depletion process for making avermectin/zein compositions which comprises contacting avermectin and zein with acetic acid, emulsifying the avermectin/zein/acetic acid solution in a mineral oil with a specific gravity of about 0.83 to about 0.88 at 25° C. and fractionated lecithin to form a dispersed phase consisting of the avermectin/zein and acetic acid and a continuous phase consisting of the mineral oil and fractionated lecithin, saturating the continuous phase with acetic acid before or during emulsification, pumping and recycling the resulting emulsion through a semi-permeable membrane which retains the dispersed phase and releases the solvent-saturated continous phase as permeate and which has a pore size of about 0.1 to about 0.8 microns, and adding additional continuous phase which is not saturated with acetic acid, resulting in depletion of the acetic acid from the dispersed phase, thereby making the avermectin/zein composition suspended in a mineral oil solution.

13. The process of claim 12, wherein the avermectin compound has the structural formula:

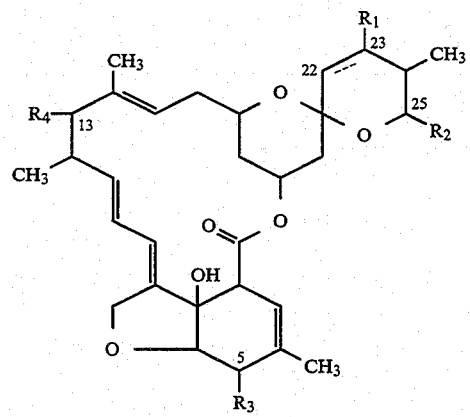

where the broken line indicates a single or a double bond at the 22,23-positions;

$R_1$ is hydrogen or hydroxy, and is hydroxy only when the broken line indicates a single bond;

$R_2$ is alkyl of from 1 to 6 carbon atoms or alkenyl of from 3 to 6 carbon atoms or cycloalkyl of from 3 to 6 carbon atoms;

$R_3$ is hydroxy, methoxy, or $=NOR_5$;

$R_5$ is hydrogen or $C_1$–$C_3$ alkyl; and $R_4$ is hydrogen, hydroxy, ($C_1$–$C_3$ alkoxy)(—$C_0$–$C_3$ alkoxy)methoxy,

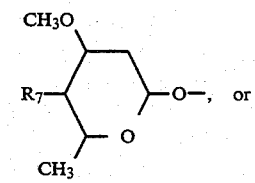

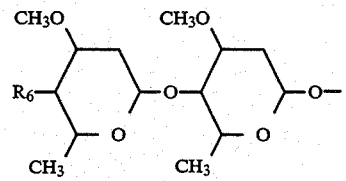

where $R_6$ and $R_7$ is=O, hydroxy, or $R_8R_9$-amino, and $R_8$ and $R_9$ are independently hydrogen, $C_1$–$C_3$ alkyl, $C_2$–$C_3$ alkanoyl, substituted benzenesulfonyl wherein the substituent is halogen or $C_1$–$C_3$ sulfonyl.

* * * * *